(12) United States Patent
Mohammadi

(10) Patent No.: US 10,849,575 B2
(45) Date of Patent: Dec. 1, 2020

(54) COMPUTER TOMOGRAPH

(71) Applicant: ESSPEN GmbH, Erlangen (DE)

(72) Inventor: Zahra Mohammadi, Erlangen (DE)

(73) Assignee: ESSPEN GmbH, Erlangen (DE)

( * ) Notice: Subject to any disclaimer, the term of this patent is extended or adjusted under 35 U.S.C. 154(b) by 28 days.

(21) Appl. No.: 16/349,244

(22) PCT Filed: Nov. 13, 2017

(86) PCT No.: PCT/EP2017/001316
§ 371 (c)(1),
(2) Date: Jul. 17, 2019

(87) PCT Pub. No.: WO2018/086744
PCT Pub. Date: May 17, 2018

(65) Prior Publication Data
US 2020/0187882 A1    Jun. 18, 2020

(30) Foreign Application Priority Data

Nov. 12, 2016   (DE) .......................... 10 2016 013 533

(51) Int. Cl.
*A61B 6/00* (2006.01)
*H01J 35/12* (2006.01)
(Continued)

(52) U.S. Cl.
CPC ............ *A61B 6/4014* (2013.01); *A61B 6/035* (2013.01); *A61B 6/4405* (2013.01); *A61B 6/587* (2013.01);
(Continued)

(58) Field of Classification Search
CPC ..... A61B 6/4014; A61B 6/035; A61B 6/4405; A61B 6/4028; A61B 6/4007; A61B 6/032;
(Continued)

(56) References Cited

U.S. PATENT DOCUMENTS 5,541,975 A * 7/1996 Anderson ............. H01J 35/106
378/130
7,568,836 B2   8/2009 Bailey et al.
(Continued)

FOREIGN PATENT DOCUMENTS

DE          2852968 A1     6/1980
DE    102008025524 A1     7/2009
(Continued)

OTHER PUBLICATIONS

Wang: Theme issue: inorganic nanotubes and nanowires, Royal Society of Chemistry, Journal of Materials Chemistry, 19(7): 826-827 (2009).
(Continued)

*Primary Examiner* — Kiho Kim
(74) *Attorney, Agent, or Firm* — Merchant & Gould P.C.

(57) ABSTRACT

A computer tomograph (1) for X-ray imaging includes a rotationally fixed gantry (2) that is displaceable at most in the axial direction (z). A plurality of X-ray emitters (3) and X-ray detectors (4) is arranged in the gantry (2) in a fixed manner about a central geometrical axis (z), in each case opposite to one another and offset with respect to each other in the direction of the central axis (z). The X-ray emitters (3) have cathodes (5) as electron emitters, which are separately connected to emitter controls (25) and cooperate with a common extraction grid (26) connected upstream of at least one focusing electrode (27). In comparison to conventional computer tomographs having rotating or rigidly arranged technical X-ray components, the computer tomograph (1) has a light and compact design.

15 Claims, 7 Drawing Sheets

(51) Int. Cl.
*A61B 6/03* (2006.01)
*H01J 35/06* (2006.01)

(52) U.S. Cl.
CPC ............ *H01J 35/065* (2013.01); *H01J 35/13* (2019.05); *H01J 2235/068* (2013.01)

(58) Field of Classification Search
CPC ........ A61B 6/587; H01J 35/13; H01J 35/065; H01J 2235/068
See application file for complete search history.

(56) References Cited

U.S. PATENT DOCUMENTS

| | | |
|---|---|---|
| 7,751,528 B2 | 7/2010 | Zhou et al. |
| 2005/0147201 A1* | 7/2005 | Hoffman ................ A61B 6/482 378/15 |
| 2007/0274456 A1 | 11/2007 | Holt |
| 2015/0282774 A1 | 10/2015 | Lee et al. |
| 2015/0305697 A1 | 10/2015 | Tamura et al. |
| 2015/0312998 A1 | 10/2015 | Tamura et al. |

FOREIGN PATENT DOCUMENTS

| | | |
|---|---|---|
| DE | 102013203541 A1 | 9/2014 |
| DE | 102011076912 B4 | 8/2015 |
| DE | 112014003207 T5 | 4/2016 |
| EP | 0488888 B1 | 7/1998 |
| EP | 1324697 B1 | 5/2006 |
| EP | 1617764 B1 | 10/2011 |
| WO | 2006/015356 A2 | 2/2006 |
| WO | 2007/038306 A2 | 4/2007 |
| WO | 2007/117677 A2 | 10/2007 |
| WO | 2009/115982 A1 | 9/2009 |
| WO | 2014/076693 A1 | 5/2014 |
| WO | 2018/086737 A1 | 5/2018 |

OTHER PUBLICATIONS

International Search Report and Written Opinion for PCT/EP2017/001316, dated Jul. 13, 2018.
International Preliminary Report on Patentability for PCT/EP2017/001316, dated May 14, 2019.

* cited by examiner

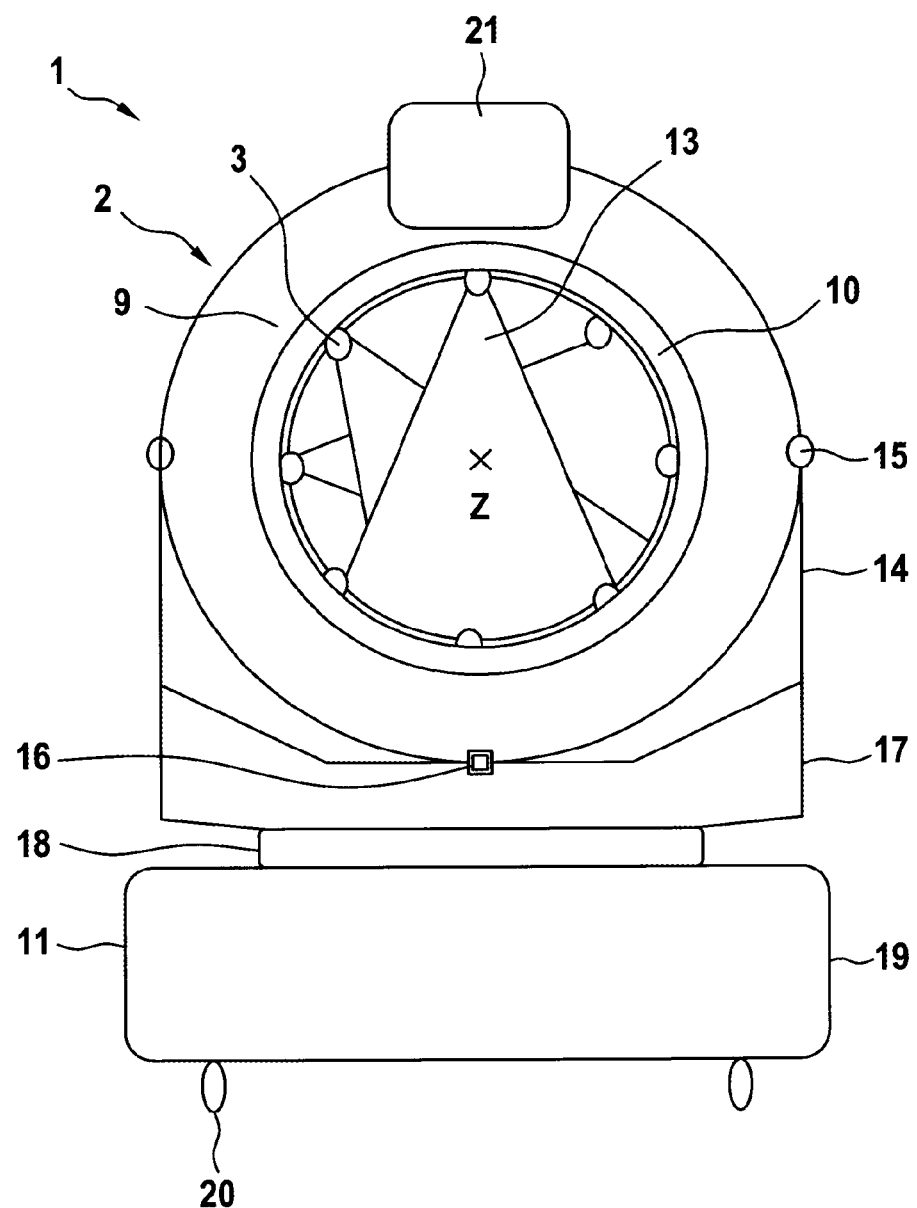
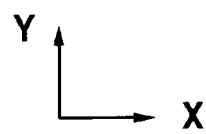

COMPUTER TOMOGRAPH

This application is a National Stage Application of PCT/EP2017/001316, filed Nov. 13, 2017, which claims the benefit of priority to German Patent Application No. 10 2016 013 533.6, filed Nov. 12, 2016, which applications are incorporated herein by reference. To the extent appropriate, a claim of priority is made to each of the above disclosed applications.

BACKGROUND OF THE INVENTION

The invention relates to a computer tomograph in which synchronous rotation of the X-ray emitter with an X-ray detector is not required for X-ray imaging. The invention further relates to a method for operating such a computer tomograph.

The gantry is the core component of conventional computer tomographs. At least one X-ray tube and, directly opposite, detectors for signal reception rotate inside the gantry housing. The imaging X-ray radiation is generated by means of high voltage in the X-ray tube. The so-called X-ray generator contains the entire control and monitoring system. Measuring data obtained, also called raw data, is collected and transmitted to a computer unit, where it is reconstructed into diagnosable images immediately following exposure. Thanks to the rapid development of information technology, high-performance computers can provide this computing power. Special cards can be inserted into multi-row spiral computer tomographs, which have faster signal processors to perform image generation in just a few seconds.

Computer tomographs having a rotating X-ray source and associated detector are disclosed, for example, in documents DE 11 2014 003 207 T5, EP 1 617 764 B1, U.S. Pat. No. 7,568,836 B2, WO 2006/015356 A2, and WO 2007/117677 A2.

A dual-source CT system in which two radiation bundles are each delimited by diaphragms such that these radiation bundles are free of mutual points of intersection at least in the examination object, is known from DE 10 2013 203 541 A1. The diaphragms can generically be called radiation influencing means. The source-detector systems including the diaphragms are rotating components of the dual-source CT system.

EP 1 324 697 B1 discloses a CT scanner which is said to provide time-coherent large-area coverage. In this case, there are three rotatable X-ray source-detector arrays, wherein the various X-ray sources are displaced relative to each other in the direction of the axis of rotation.

DE 28 52 968 A1 discloses a device called "tomographic apparatus for producing transverse layer images of a radiography subject". This device likewise comprises three source-detector arrays which can be rotated jointly and which are arranged at an offset to each other in the direction of their joint axis of rotation.

Another tomographic system having components which rotate about a longitudinal axis of the tomograph is known from EP 0 488 888 B1. Two carriages, each of which carrying an X-ray source and a two-dimensional sensor grid, rotate simultaneously, such that the carriages are constantly diametrically opposed.

US 2015/0305697 A1 discloses a tomographic device in which the source-detector array is rigid but the filter array can be rotated. The source array includes a multitude of X-ray sources, which are disposed in form of a ring around the volume to be examined. A multitude of, for example, 1,000 extraction grids may be provided, each of which being associated with an electron source. This is said to enable radiograms from 1,000 different directions, wherein each extraction grid can be controlled separately. Simultaneously with controlling the extraction grids arranged in a ring shape, the filter array, that is, an arrangement of radiation influencing means, must be rotated about the central axis of the tomographic device. US 2015/0305697 A1 proposes carbon or silicon nanotubes as electron-emitting materials.

SUMMARY OF THE INVENTION

Computer tomographs with a rotating gantry or other rotating components, such as filter components, have considerable disadvantages. A complex mechanism requiring much space is needed for uniform and geometrically precise rotation. The mechanical rotation further requires relatively slow rotational speeds and therefore a longer exposure time, even if multiple pairs of X-ray sources and detectors arranged opposite each other are provided in a gantry. Such devices have very high manufacturing costs and, since the mechanical system is susceptible to failure, very high maintenance costs.

Its high power consumption and enormous space requirement should be particularly noted, such that mobile deployment of such computer tomographs, e.g. in ambulances or field hospitals, is possible at best with a great technological effort.

To remedy the disadvantages mentioned, a fixed arrangement of X-ray emitters connected in series was proposed instead of a rotating gantry. In such a computer tomograph, the X-ray emitters are directed at the body to be examined and are each controlled separately. Sequential control of X-ray emitters thus replaces the rotation of an X-ray tube, which had been required as yet. An arrangement of separately controllable X-ray emitters connected in series is also described, for example, in DE 10 2011 076 912 B4.

Computer tomographs having a fixed array of X-ray emitters can particularly use X-ray emitters which are configured as field emission X-ray tubes. Such X-ray emitters may for example comprise cathodes containing carbon nanotubes. A stationary computer tomograph of this design, which is particularly intended for radiograms of the female breast, is described in U.S. Pat. No. 7,751,528 B2, X-ray imaging for medical diagnostics using computer tomography has been established in the meantime. Computer tomography often is the first and therefore most important means of choice, for example, in patients with suspected stroke or generally for head injuries. Computer tomography has also proved its worth in materials testing, e.g. for irradiating suspicious objects.

It is the problem of the invention to provide a computer tomograph which is developed further compared to prior art, which is generally suited for X-ray imaging, and which can also be used as a mobile device, for example, in ambulances and field hospitals.

This problem is solved, according to the invention, by a computer tomograph. This problem is likewise solved by a method for operating a computer tomograph. Embodiments and advantages of the invention explained below in conjunction with the operating method apply accordingly to the device, that is, the computer tomograph, and vice versa.

The proposed computer tomograph for X-ray imaging comprises a rotationally fixed gantry. The gantry represents an assembly in which a plurality of X-ray emitters and a plurality of X-ray detectors are fixedly arranged about a central geometrical axis, namely, opposite each other and at an offset from each other in the direction of said central axis.

Furthermore, the gantry includes radiation influencing means, that is, focusing electrodes, which are also arranged at a fixed angular orientation and thus at a fixed position relative to the X-ray emitters and X-ray detectors in the computer tomograph. Multiple electron emitters, i.e. cathodes, which are provided for emitting electrodes and, if said electrodes hit an anode, ultimately for generating X-ray radiation, interact with a common extraction grid. For example, eight or 24 cathodes can be arranged on a common extraction grid. In an extreme case, a single X-ray tube with a multitude of cathodes just comprises a single extraction grid.

Compared to X-ray equipment in which each cathode is associated with a separate extraction grid, which must be controlled separately, as for example in US 2015/0305697 A1, the equipment outlay in the computer tomograph according to the invention is dramatically reduced. However, this computer tomograph may still comprise a plurality of electron emitters and a matching number of X-ray emitters, particularly more than 100, for example between 200 and 400. In addition, the need is eliminated to rotate components during operation of the computer tomograph, e.g. a source-detector array and/or a filter array.

The X-ray emitters are provided for directed emission, and the associated X-ray detectors are provided for detection of X-rays as radiation bundles. These radiation bundles have a direction of maximum intensity of the emitted X-ray radiation, wherein said direction will be called principal emission direction below. Such a principal emission direction is present in all X-ray sources which are different from a spherical radiation source. In the proposed computer tomograph, the geometrical shape of the radiation bundle can be adjusted by the design of the X-ray source of the respective X-ray emitter and by radiation influencing means. The term "radiation influencing means" can generally refer to electron beams and/or X-rays. The term of radiation influencing means includes focusing electrodes, that is, means for influencing the electron beam, but also diaphragms and filters, which act on the X-ray radiation. For example, the proposed computer tomograph features a radiation bundle in the shape of a cone or a fan. For example, an X-ray source in the form of a focal spot is configured as a point source or a line source or a delimited area on a carrier device in the proposed computer tomograph.

The arrangement of the X-ray emitters on the one hand and the X-ray detectors on the other hand at an offset from each other relative to the central axis of the computer tomograph is accompanied by the fact that the principal emission direction of each X-ray source intersects the central axis at an angle different from 90°.

In the proposed computer tomograph, an X-ray emitter and at least one X-ray detector arranged opposite said emitter are electrically controlled sequentially for taking a radiogram. This process replaces a mechanical rotation of X-ray sources and detectors. The examination object is placed lying between the X-ray emitters and the X-ray detectors.

For example, a radiogram can be taken in that adjacent X-ray emitters are electrically controlled sequentially, one after the other, together with an X-ray detector arranged on the opposite side. Likewise, X-ray emitters and associated X-ray detectors can be operated in any other sequence, wherein said sequence is also variable within each displacement step. A specific region of a cross section to be examined by X-ray radiation (ROI=region of interest) can be selected by controlling only those X-ray emitters and X-ray detectors which are directed at the ROI. Computer-aided methods such as tomosynthesis or filtered back-projection (FBP) can be used to generate cross sectional views and volume structures from the radiograms obtained in this manner, which are projection images.

For a projection, only that frame area is selected which contains essential information, i.e. data, for computer-aided image generation. Artifacts and areas with poor resolution are avoided. This significantly shortens the time needed for computer-aided image generation. Computer-aided image generation can also be performed fast on computers with less computing power, and image resolution can be improved when using a single detector rather than a plurality of X-ray detectors.

Therefore, the proposed computer tomograph can produce high-resolution radiograms with a minimal design effort and shorter exposure time compared to prior art. The image resolution achievable in the entire ROI is the higher the more a plurality of X-ray emitters and X-ray detectors is fixedly arranged opposing each other in the gantry.

The computer tomograph is particularly suitable for performing a method having the following steps:
  Generating, by the computer tomograph, a first set of projection images taken from different projection directions,
  Taking at least one additional set of projection images, wherein the projection directions at least partially match the projection directions of the first set of projection images,
  Determining the level of similarity between two projection images taken from matching projection directions,
  Generating other projection images, wherein the frequency of selected projection directions depends on the level of similarity of projection images taken from the respective projection directions at subsequent points in time.

The examination object may include the body to be examined, particularly a body part of a patient, but also other objects, such as surgical kits, which are present in the volume under examination.

Since the frequency of the angular setting chosen for projection images with respect to the angular position of the X-ray emitter controlled inside the gantry depends on the degree of changes projection images taken one after the other from said angular position show, the number of projection images required for generating meaningful slice images can be minimized, even for slice images which change fast over time. Projection images are created from a specific projection direction the more often the lower the level of similarity between projection images taken from that respective projection direction at subsequent points in time. The angular relations between X-ray emitters which are controlled one after the other are not predetermined but result from an analysis of the projection images during the operation of the computer tomograph.

In general, the number of X-ray emitters in the proposed computer tomograph is at least equal to the number of projections for such computer-aided image generation. If multiple X-ray detectors are associated with an X-ray emitter, more than one projection image can be generated with that X-ray emitter.

In addition to assigning an individual X-ray emitter to just a specific number of X-ray detectors, the invention is based on the idea of an arrangement of the respective X-ray emitters and X-ray detectors at an offset from each other in the direction of the central axis.

Such an arrangement can avoid dead spots about the axial direction. If X-ray emitters and X-ray detectors are arranged in an arc of more than 180° about the axial direction, for example, this is only possible if the X-ray emitters and X-ray detectors are at an axial offset. It is only possible to arrange X-ray emitters and X-ray detectors such that they completely enclose the axial direction and thus the intended region of interest using the proposed computer tomograph, which has this critical design feature. In the proposed computer tomograph having this design feature, both the array geometries of the X-ray emitters and the X-ray detectors can be freely selected about the axial direction.

In a class of embodiments of the proposed computer tomograph, the X-ray emitters are arranged in a circle and the X-ray detectors are arranged at angular dispositions about the axial direction. If the proposed computer tomograph is intended for examining the human breast or for materials testing of workpieces, for example, it is not necessary that the X-ray emitters or X-ray detectors completely enclose the central axis.

For example, the gantry is mounted on a device base in the proposed computer tomograph. Expediently, devices for power supply and electronic control and the computer are installed in the device base. The proposed computer tomograph can be implemented particularly easily in a preferred design as a portable device.

When selecting an X-ray beam in the form of a cone or fan with a fan plane parallel to the central axis and sufficient width of the X-ray radiation absorption area of the X-ray detectors, the proposed computer tomograph having a stationary gantry can image an ROI in a non-moving object.

Advantageous further developments of the proposed computer tomograph are described below.

In one embodiment, the proposed computer tomograph is further developed by a gantry which can be moved towards the central axis. In this embodiment of the proposed computer tomograph, the gantry and the examination object perform a relative movement towards each other in the direction of the central axis while a radiogram is taken. To this end, the gantry may be mounted on an arrangement of straight guide rails on a device base, wherein the straight guide rails are parallel to the central axis.

This embodiment of the proposed computer tomograph can reach a coverage width in a radiogram of at least 30 cm in the direction of the central axis by moving the gantry. In this further developed embodiment, the proposed computer tomograph is particularly suited for computer tomographic X-ray imaging of the human head or breast.

For computer tomographic generation of a radiogram, the gantry can be guided in steps or, in an alternative operating mode, continuously, over the examination object towards the central axis. In each step, a radiogram is taken by sequential electric control of the individual X-ray emitters together with at least one X-ray detector arranged on the opposite side. All individual steps completely cover the ROI in the direction of the central axis. Computer-aided imaging can be used to generate cross sectional views and volume structures of the examined object from the radiograms obtained in this manner, which are projection images. This means that, in this embodiment of the proposed computer tomograph, the ROI is not just selectable by selective control of X-ray emitters and X-ray detectors, but also by the selected displacement interval of the gantry towards the central axis.

By selecting an X-ray beam in the shape of a fan, having a fan plane and a principal emission direction perpendicular to the X-ray radiation absorption area of the X-ray detector, this embodiment of the proposed computer tomograph can particularly advantageously be used to limit the X-ray exposure of the examination object to the desired geometrical segment of the ROI. Furthermore, X-ray detectors with a smaller width of the X-ray radiation absorption area can be used, which also reduces the manufacturing effort. As the number of partial geometrical sections per length of the ROI towards the central axis grows, the resolution of the cross sectional views and volume structures of the examined object generated by computer-aided imaging increases as well. In this embodiment, the proposed computer tomograph as a whole is configured as a mobile device.

In a preferred further development, the X-ray emitters and the X-ray detectors of the proposed computer tomograph completely enclose the central axis. This has the advantage that any section (ROI) of the examined object can be shown by X-ray imaging at a constant high quality.

If the X-ray emitters and X-ray detectors form a circle about the central axis, particularly uniform resolution of the radiogram is achieved. In this embodiment, the proposed computer tomograph is particularly suited for X-ray imaging of the human head. It is particularly advantageous that a ROI can be freely selected in all directions about the axial direction, i.e. the longitudinal axis of the computer tomograph, at a high quality and high resolution, even if only a part of the X-ray emitters is controlled.

A circular arrangement of the individual X-ray emitters and detectors is not absolutely necessary to achieve a high resolution. In another embodiment of the proposed computer tomograph, the individual X-ray emitters or detectors are arranged about the central axis in three similar rows, particularly rows of the same length, which rows form a regular polygon. The resolution of the X-ray image is the better the more sides regular polygon has in which the multi-emitter array or the multi-detector array is arranged. But the manufacturing effort increases with the number of rows as well. A hexagon or octagon or decagon have proved optimal polygons with respect to the resolution of the radiogram and the manufacturing effort.

Advantageous embodiments of the x-ray emitters and the X-ray detectors of the proposed computer tomograph are described below.

The X-ray emitters in the gantry preferably comprise cathodes for field emission of electrons, wherein the cathodes contain carbon nanotubes. The carbon nanotubes serve as cold cathodes to generate electrons, which are then accelerated to be shot at the anode as the actual X-ray source of the X-ray emitter. In this further development of the proposed computer tomograph, the X-ray emitters are configured as field emission X-ray emitters. An imaging X-ray beam is generated on the anode by electronically switching a single cathode on and off. Such X-ray emitters can be configured particularly small and deposited on a joint carrier, which is enclosed by a single vacuum tube; such an arrangement is a multibeam field emission X-ray (MBFEX) tube, which once again allows a more compact design. Carbon nanotubes have a low field emission threshold of less than 2 V $\mu m^{-1}$ for the field emission of electrons. Therefore the proposed computer tomograph can be run with a power supply unit having a relatively low output.

Carbon nanotubes are generically called nanorods. Instead of carbon nanotubes or in addition to carbon nanotubes, electron emitters of the computer tomograph may comprise other nanorods. Nanorods may comprise an intrinsically homogeneous or heterogeneous composition and may either be configured as hollow bodies, that is, tubes, or as solid bodies.

For example, nanorods, particularly nanotubes, can be formed of metal oxides. In principle, nanorods from metal oxides—just like nanowires, which are not relevant in the present case—are known for example, from the publication titled "Theme issue: inorganic nanotubes and nanowires", Journal of Materials Chemistry, 2009, 19, pp. 826-827. This publication mentions, inter alia, $TiO_2$, $ZnO$, and $Al_2O_3$ as materials from which nanotubes may be formed.

Metal oxides, such as titanium oxide, zinc oxide, or manganese oxide, both in pure and in doped form, are suitable for producing an electron emitter which can be used in the computer tomograph according to the invention. Likewise, other materials from which nanorods are built or which are contained in nanorods, such as metals, sulfides, nitrides, or carbides may be present in pure or doped form.

If the electron emitter contains a sulfide, this can be a metal sulfide, particularly molybdenum sulfide. Nitrides of which the nanorods of the electron emitter can be fully or partially constructed particularly include boron nitride, aluminum nitride, carbon nitride, and gallium nitride. Silicon carbide is a particularly suitable carbide for producing nanorods, particularly nanotubes. Likewise, nanorods, particularly in the form of nanotubes, can be produced from silicon, optionally with doping elements.

The use of nanorods containing cerium or lanthanum is another option in the context of producing the electron emitter. In this context, we make exemplary reference to patent application WO 2014/076693 A1.

Suitable parent products for producing the nanorods, which emit electrons when the electron emitter is in operation, include rod-shaped, optionally hollow elements of polymeric materials. The nanorods of the electron emitter can be made from parent products which are completely built from polymeric materials, or from parent products which only partially comprise polymeric materials, particularly in the form of a coating.

A computer tomograph may include electron emitters of a uniform or non-uniform design. Likewise, the associated focusing electrodes can have a uniform or varying design throughout the entire computer tomograph. Thus there are four ways of combining electron emitters and focusing electrodes:

Combining uniform emitters and uniform focusing electrodes,
combining different emitters and different types of focusing electrodes.
combining emitters of different types and uniform focusing electrodes,
combining different emitters and different types of focusing electrodes.

Different emitters may differ with respect to their geometries and/or materials. The emitters, particularly in the form of emitters containing carbon nanotubes, can be produced at a consistent high quality. Details of the potential manufacture of the emitters are disclosed in patent application no. 10 2016 013 279.5 filed with the German Patent and Trademark Office (DPMA) and in the PCT application which claims the priority of said application and was filed with EPO on Nov. 8, 2017. Such emitters are particularly characterized by extremely minor aging effects.

It is also possible to use dispenser cathodes, as they are basically known, for example, from DE 10 2011 076 912 B4.

Bundles of electron beams, starting from the electron emitters, passing through the extraction grid, and influenced by focusing electrodes impinge on an anode, a preferred embodiment of which is configured as a rigid, liquid-cooled anode. A coolant, particularly in the form of a conductive oil, flows preferably concentrically with the central axis of the elongate, rod-shaped, or curved anode through a duct with an annular cross section which is formed within the anode. Another duct through which the coolant is guided back is located in the center of said duct in this embodiment. The anode thus has the shape of a cooling finger at the end of which the introduced coolant is redirected.

The anode is under high voltage of the order of 100 kV when the computer tomograph is in operation. In addition to varying the emission current of the cathodes, the anode voltage can be varied, wherein both variables—emission current and anode voltage—can be changed very fast. A multitude of different settings of operating parameters of the computer tomograph can be made in one and the same examination by multiplying the two variable parameters of emission current and anode voltage. This relates to both the frequency of the X-ray radiation emitted and the X-ray dose emitted per pulse. Instead of a dual energy CT system, as known in principle from the prior art cited above, the computer tomograph therefore is a multi-energy computer tomograph. The X-ray radiation emitted, for example, is varied by at least 100 steps in wavelength and dose per pulse during the examination of an examination object. It is also particularly advantageous that the X-ray detectors including the associated analytical equipment can be of a particularly simple design compared to conventional dual-energy systems, which perform measurements relating to two different wavelengths using said detectors.

The X-ray detectors in the gantry are for example configured as photon counting detectors or as separate flat screen detectors for X-rays or as separate photodiodes, such as direct solid-state detectors (SSD). This allows particularly simple electronic control of the X-ray detectors together with their respective associated X-ray emitters.

The X-ray detectors preferably comprise direct solid-state detectors for detecting X-ray radiation. If the X-ray detectors are configured as flat screen detectors, they convert X-ray signals into electrical signals for each pixel on the X-ray radiation absorption area. A radiogram can then be generated from these electrical signals. Such X-ray detectors allow a very high resolution of the radiogram. Such X-ray detectors can also easily be integrated in a joint array, said array representing a detector assembly.

In a particularly preferred embodiment of the proposed computer tomograph, the X-ray emitters are arranged in a MBFEX tube and the X-ray detectors are fixedly arranged in a detector assembly in the gantry. The MBFEX tube and the detector assembly are arranged relative to each other such that the principal emission direction of each anode of each X-ray emitter intersects the central axis at an angle which is different from 90°. Thus, each X-ray emitter and each X-ray detector are arranged at an offset relative to each other in the direction of the central axis of the computer tomograph. In this further developed embodiment, the proposed computer tomograph can be implemented in a particularly compact and stable design.

When using X-ray detectors with a high frame rate and full resolution, a complete set of high-resolution projection images can be created in less than 20 seconds, like in a standard CT. This means that the proposed computer tomograph can provide a high-resolution radiogram in just a few seconds, which is particularly advantageous when dealing with restless patients.

Unlike prior art computer tomographs in which the X-ray source and a detector are rotatably arranged, focal spot enlargement about the axial direction due to moving components in excluded by the operating principle in radiograms made with the proposed computer tomograph.

The proposed computer tomograph, particularly its further developments, are characterized by a very compact and robust design. It is particularly advantageous that the patient does not have to be moved through the gantry for a radiogram.

The proposed computer tomograph, particularly with X-ray emitters comprising cathodes with carbon nanotubes, has the following advantages compared to the computer tomographs which are currently available in the market:

Reduced radiation dose for the patients;
Increased sensitivity and specificity of imaging devices;
Higher output;
Less weight and smaller footprint;
Improved mobility for surgeons/physicians;
Complete care for needier patients;
Improved quality or reduced costs (particularly purchasing and operating costs for such medical imaging systems) for health care providers.

The use of the proposed computer tomograph is by no means limited to medical diagnostics. The proposed computer tomograph is for example also suitable for X-ray imaging of inanimate objects, for example for workpiece testing or product testing or for checking the contents of closed containers.

BRIEF DESCRIPTION OF THE DRAWINGS

The proposed computer tomograph will be explained in more detail below with reference to a drawing which summarizes multiple embodiments. Wherein:

FIG. 1 shows a cross section of a computer tomograph 1 perpendicular to the central axis z of its gantry 2;

Figure 2:
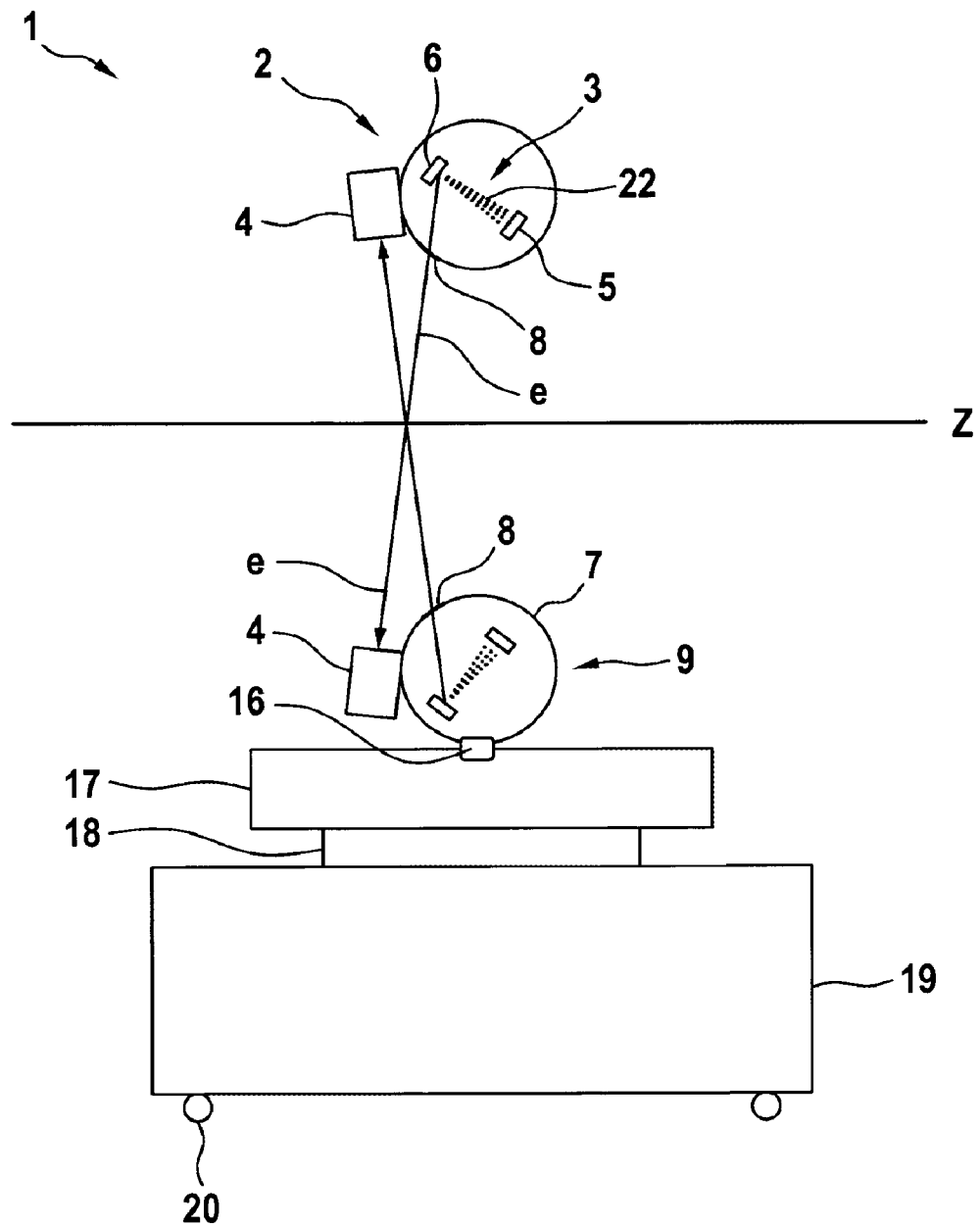
FIG. 2 shows a cross section of a computer tomograph 1 parallel to the central axis z of its gantry 2.

All exemplary embodiments of the computer tomograph 1 which are explained below with reference to a drawing comprise a rotationally fixed gantry 2. A plurality of X-ray emitters 3 and X-ray detectors 4 is arranged in the gantry 2 in a fixed manner, that is, not rotatable, about a geometrical center axis z, in each case opposite to one another and offset with respect to each other in the direction of the center axis z. In all exemplary embodiments, an X-ray emitter 3 is sequentially electrically controlled together with an X-ray detector 4 arranged opposite the emitter for taking a radiogram.

In all exemplary embodiments, the X-ray emitters 3 comprise cathodes 5 for field emission of electrons to generate electrons which then are accelerated to be shot at the anode 6 as the actual X-ray source of the respective X-ray emitter 3. The cathodes 5 of the X-ray emitters 3 contain carbon nanotubes. The X-ray emitters 3 are thus configured as separate field emission X-ray emitters. The X-ray emitters 3 are fixedly mounted on a joint carrier and installed in a vacuum tube 7. X-ray windows 8 are inserted in the vacuum tube 7 through which the X-ray radiation generated can exit. This arrangement of the X-ray emitters 3 corresponds to a MBFEX tube 9.

In all exemplary embodiments, the X-ray detectors 4 are configured as flat screen detectors which comprise direct solid-state detectors for detecting X-ray radiation. The X-ray detectors 4 are fixedly arranged in a detector 10.

In all exemplary embodiments of the computer tomograph 1, the respective MBFEX tube 9 and the detector assembly 10 are fixedly arranged in the gantry 2 in such a manner that the principal emission direction e of each anode 6 of each X-ray emitter 3 intersects the central axis z at an angle which is different from 90°.

All embodiments of the proposed computer tomograph 1 are intended as portable devices for computer tomographic X-ray imaging of a patient's body parts, particularly of the head and the breast. When a radiogram of a human limb or a human head or a human breast is taken, said body part is located between the X-ray emitters 3 and the X-ray detectors 4, preferably in the region about the central axis z.

In all exemplary embodiments, the gantry 2 is mounted on a device base 11. An electronic multichannel control system 12 is installed in the device base 11, wherein the electronic multichannel control system 12 is provided for controlling the computer tomograph 1, the X-ray emitters 3 and the X-ray detectors 4, collecting the data for X-ray imaging and computer-aided image generation, for data storage and for data output an radiogram output.

DETAILED DESCRIPTION OF THE PREFERRED EMBODIMENTS

FIG. 1 shows a cross section of a first exemplary embodiment of the computer tomograph 1 perpendicular to the central axis z of its gantry 2 with a view to the X-ray emitters 3 in the MBFEX tube 9. The X-ray emitters 3 are arranged in a full circle about the central axis z, and the MBFEX tube 9 also has a respective circular configuration. The cathodes 5 and the anodes 6 of the X-ray emitters 3 and the vacuum tube 7 are not visible in FIG. 1. The X-ray detectors 4 are also not visible in FIG. 1 and installed in the detector assembly 10, wherein the detector assembly 10 in this exemplary embodiment is also arranged in a full circle about the central axis z. In this exemplary embodiment, the central geometrical axis z extends through both circle center points of the MBFEX tube 9 and detector assembly 10 or the respective arrays of X-ray emitters 3 and X-ray detectors 4, such that in this exemplary embodiment the positions of both circle center points define the extension of the central axis z.

In this exemplary embodiment, the anodes 6 of each X-ray emitter 3 are designed in such a manner that they each only generate one X-ray fan beam 13 having a fan plane and principal emission direction e perpendicular to the X-ray radiation absorption area of the respective X-ray detector 4.

In this exemplary embodiment, every ROI in the inner region of the gantry 2 about the central axis z can thus be imaged completely, at a high resolution, and at the same time with a relatively low X-ray exposure of the object examined, as is illustrated by the X-ray fan beam 13 of the emitted X-ray radiation shown for various X-ray emitters 3. The proposed computer tomograph in this exemplary embodiment, particularly its gantry 2, is characterized by an extremely compact design.

The device base 11 of the computer tomograph 1 in this exemplary embodiment comprises a holder 14 with two pivot points 15 and a locking device 16, a displacement device 17, a lifting device 18, and a housing 19 on lockable castors 20. The gantry 2 is pivotably mounted to the device base 11 at the pivot points 15 of the holder 14 and can be locked by means of the locking device 16. The holder 14 is mounted onto the displacement device 17, wherein the displacement device 17 is provided for displacing the gantry 2 in the direction of the central axis z. The lifting device 18, which is mounted onto the housing 19, is provided for height adjustment of the gantry 2 before making a computer tomographic radiogram of a human head. The electronic multichannel control system 12 is installed in the housing 19. A screen 21 is mounted to the gantry 2, which screen is provided for operating the multichannel control system 12 and for displaying the radiogram generated by computer tomography. The computer tomograph 1 is designed as a mobile device in this exemplary embodiment and can be moved on the lockable castors 20 to any desired location.

The displacement device 17 comprises an arrangement of straight guide rails and an electric motor. The straight guide rails are parallel to the central axis z. The gantry 2 can be moved along the guide tracks in the direction of the central axis z by means of the electric motor. The guide rails and the electric motor are not visible in FIG. 1. In this embodiment of the proposed computer tomograph 1, the gantry 2 and the examination object perform a relative movement towards each other in the direction of the central axis z while a radiogram, for example of the human head, is taken. For computer tomographic generation of a radiogram, the gantry 2 can be guided in steps or, in an alternative operating mode, continuously over the examination object towards the central axis z. In each step, a radiogram is taken by sequential electric control of the individual X-ray emitters 3 together with at least one X-ray detector 4 arranged opposite said emitter. All individual steps completely cover the ROI in the direction of the central axis z. In this exemplary embodiment, a coverage width of 30 cm in the direction of the central axis z can be achieved for radiograms. When taking such a radiogram with incremental displacement of the gantry 2, the gantry 2 is locked by means of the locking device 16.

For a computer tomographic radiogram of the human breast, the locking device 16 is released and the gantry is pivoted by 90° with respect to the illustration in FIG. 1, and the displacement device 17 is locked. This corresponds to pivoting the central axis z by 90°. The gantry 2 can thus be displaced in the direction of the central axis z using the lifting device 18. A computer tomographic radiogram of the human breast is taken, for example, in that a female patient is lying on a couch having a cutout, wherein the patient's breast is placed in the cutout of the couch and between the X-ray emitters 3 and X-ray detectors 4.

FIG. 2 shows the same exemplary embodiment as FIG. 1, wherein the computer tomograph 1 is shown in a cross section parallel to the central axis z of its gantry 2. FIG. 2 shows an example of the projection of the electron beam 22 generated using the cathode 5 onto the anode 6 and the principal emission directions e of the X-ray radiation generated. FIG. 2 is not to scale. The holder 14 with the two pivot points 15 is not visible in FIG. 2.

Figure 3:
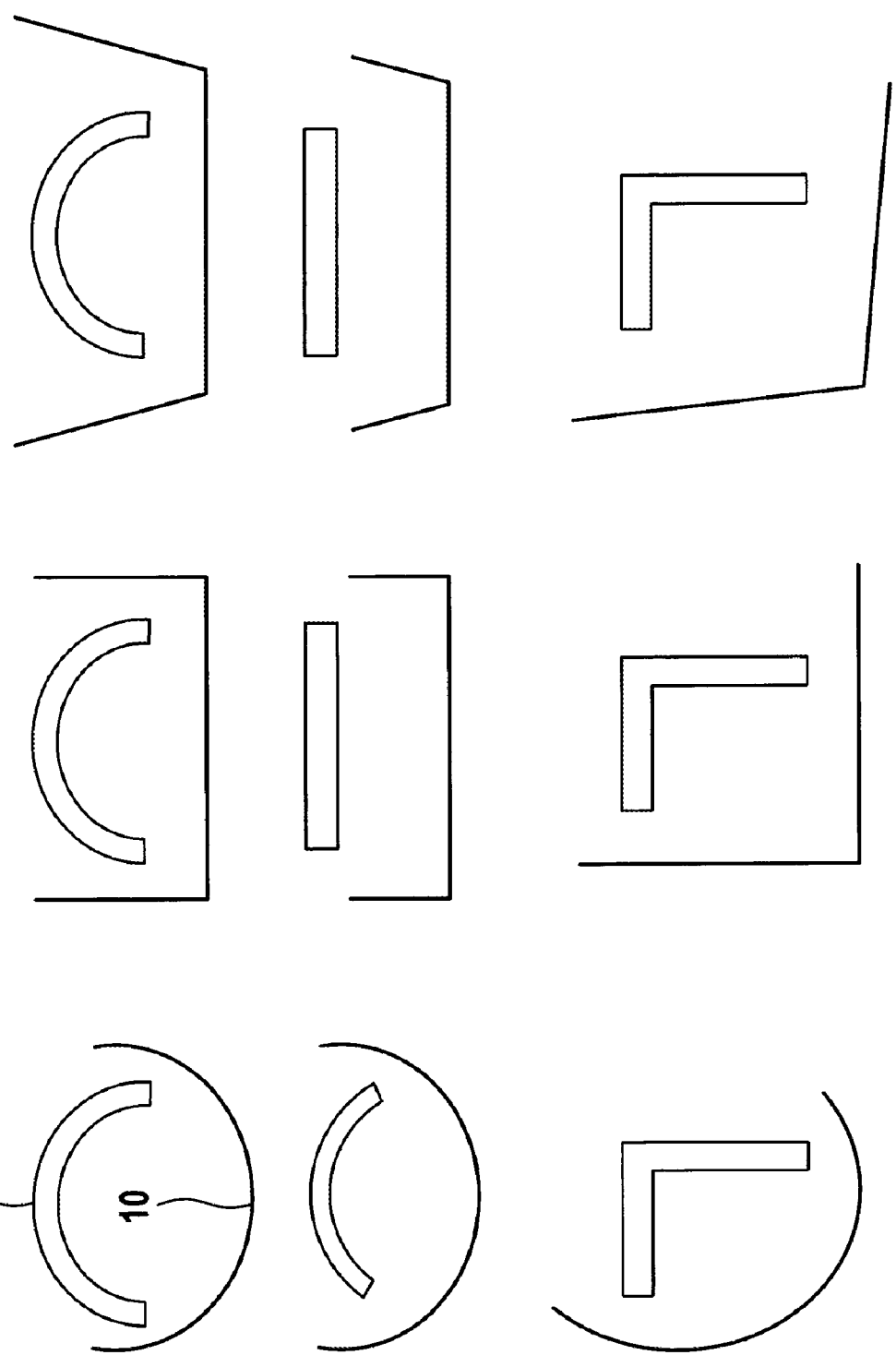
FIG. 3 shows schematic views of various embodiments of a computer tomograph 1 with respect to arrays of X-ray emitters 3 and X-ray detectors 4.

FIG. 3 shows a schematic view of various embodiments of a computer tomograph 1 with respect to the arrangements of X-ray emitters 3 and X-ray detectors 4 relative to each other. The geometries of the respective MBFEX tubes 9 and the detector assembly 10 correspond to the respective array geometries of the X-ray emitters 3 and X-ray detectors 4. As is visible from the illustrations, the MBFEX tube 9 can have a curvilinear, straight, or bent shape. The detector assembly 10 can also be curvilinear. Likewise, the detector assembly 10, which is only shown as a line in the pictogram-like representations in FIG. 3, can be bent one or multiple times. The detector assembly 10 may also be completely flat, which is generally known but not shown herein.

Figure 4:
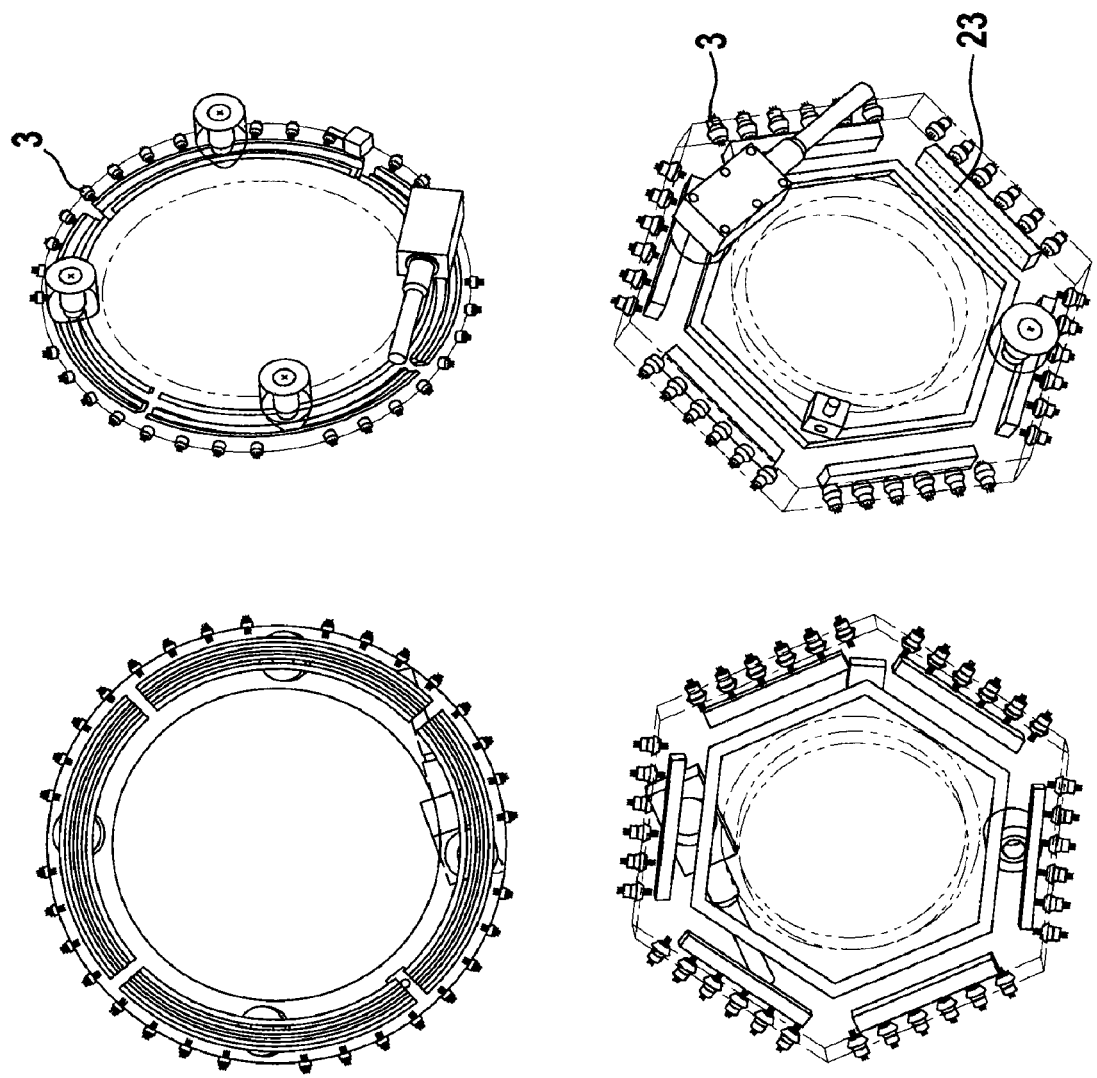
FIG. 4 shows two embodiments of a computer tomograph 1 with X-ray emitters 3 and X-ray detectors 4 which fully enclose the central axis z.

FIG. 4 shows two exemplary embodiments of the computer tomograph 1, with views to the MBFEX tube 9. In the first exemplary embodiment (top left and right in FIG. 4), the X-ray emitters 3 in the MBFEX tube 9 are arranged in a circle about the central axis z. In the second exemplary embodiment (bottom left and right in FIG. 4), the X-ray emitters 3 in the MBFEX tube 9 are formed into a regular hexagon of six uniform rows 23, wherein six X-ray emitters 3 are arranged on each row 23. The detector assemblies 10 of the two exemplary embodiments, which belong to the respective gantries 2, are not visible in FIG. 4; but the detector assemblies 10 have the same geometries as the respective MBFEX tubes 9, wherein the array geometry of the X-ray detectors 4 matches the array geometry of the X-ray emitters 3.

Figure 5:
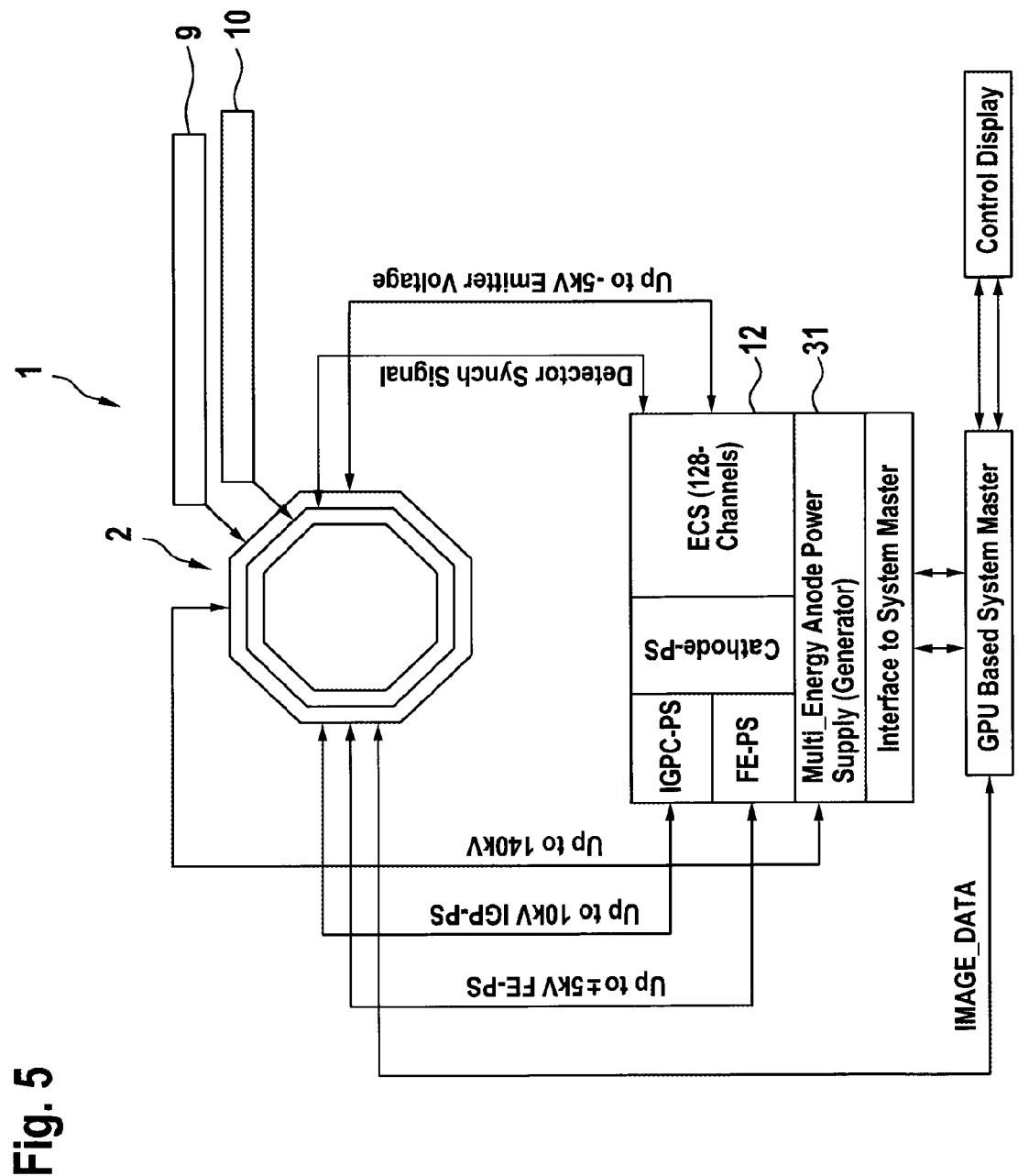
FIG. 5 shows a schematic view of an electronic multichannel control system 12 of a computer tomograph 1.

FIG. 5 shows an exemplary embodiment of the computer tomograph 1 with a schematic view of an electronic multichannel control system 12. The electronic multichannel control system 12 is provided for operating each X-ray emitter in the pulsed operating mode, wherein the electronic multichannel control system 12 comprises a high-frequency high-voltage anode power supply and a fast feedback loop between the X-ray beam and the electronic control system for current measurement to allow precise and constant dose control (mAs) from X-ray emitter 3 to X-ray emitter 3. The reconstruction algorithm is based on filtered back projection with the option to utilize the advantages of the iterative reconstruction algorithm for lowering the number of views per radiogram and for automatically reducing the exposure dose per radiogram for the patient.

In the exemplary embodiment according to FIG. 5, the gantry 2 comprises 128 X-ray emitters 3 and a multitude of X-ray detectors 4. Thus, 128 projections can be generated in this exemplary embodiment. In the MBFEX tube 9, eight uniform rows 23 of X-ray emitters 3 form a regular octagon, wherein 16 X-ray emitters 3 are arranged on each row 23. The X-ray detector assembly 10, which includes the X-ray detectors 4, is also formed into a regular octagon of eight uniform rows 23, wherein an equal number of X-ray detectors 4 is arranged on each of the rows 23. The X-ray emitters 3 and X-ray detectors 4 are not visible in FIG. 5.

Details of the MBFEX tube 9 of the computer tomograph 1 according to FIG. 1 are explained below with reference to FIG. 6.

Multiple cathodes 5, that is, electron emitters, are visible inside the vacuum tube 7, which cathodes differ in geometry and are arranged on a joint circuit board 24. Each cathode 5 is connected to a separate emitter control 25. Each of the emitter controls 25 is integrated into the electronic multichannel control system 12 and allows individual control of the cathodes 5. The cathodes 5 are operated at a negative potential.

An electron beam 22 from a cathode 5 is emitted by means of an extraction grid 26, wherein a common extraction grid 26 interacts with multiple cathodes 5. As is visible from FIG. 6, the extraction grid 26 is grounded via the electronic multichannel control system 12.

Unlike this, a focusing electrode 27, which is generally called a radiation influencing means, is grounded via the tube housing 28 of the MBFEX tube 9. Separate grounding of the extraction grid 26 and the focusing electrode 27 has advantages with respect to the operational stability of the X-ray emitter 3. There is an approximately exponential relationship between the voltage applied by the emitter control 25 to the cathodes 5 and the emission current. This means that the electrical current, which exists in the form or the electron beam 22, reacts highly sensitively to increases of the emitter voltage applied to the cathodes 5. If the emitter voltage gets into an excessive range, the electron beam 22 generates an ion bombardment from the focal spot on the anode 6, which impacts the extraction grid 26. Despite the grounding of the focusing electrode 27, this causes the potential of the focusing electrode 27 to be temporarily drawn into a positive range. Since the grounding of the extraction grid 26 is separate from the grounding of the focusing electrode 27, further repercussions on the extraction grid 26, which would result in a sudden severe increase of the emission current, are effectively suppressed.

Figure 6:
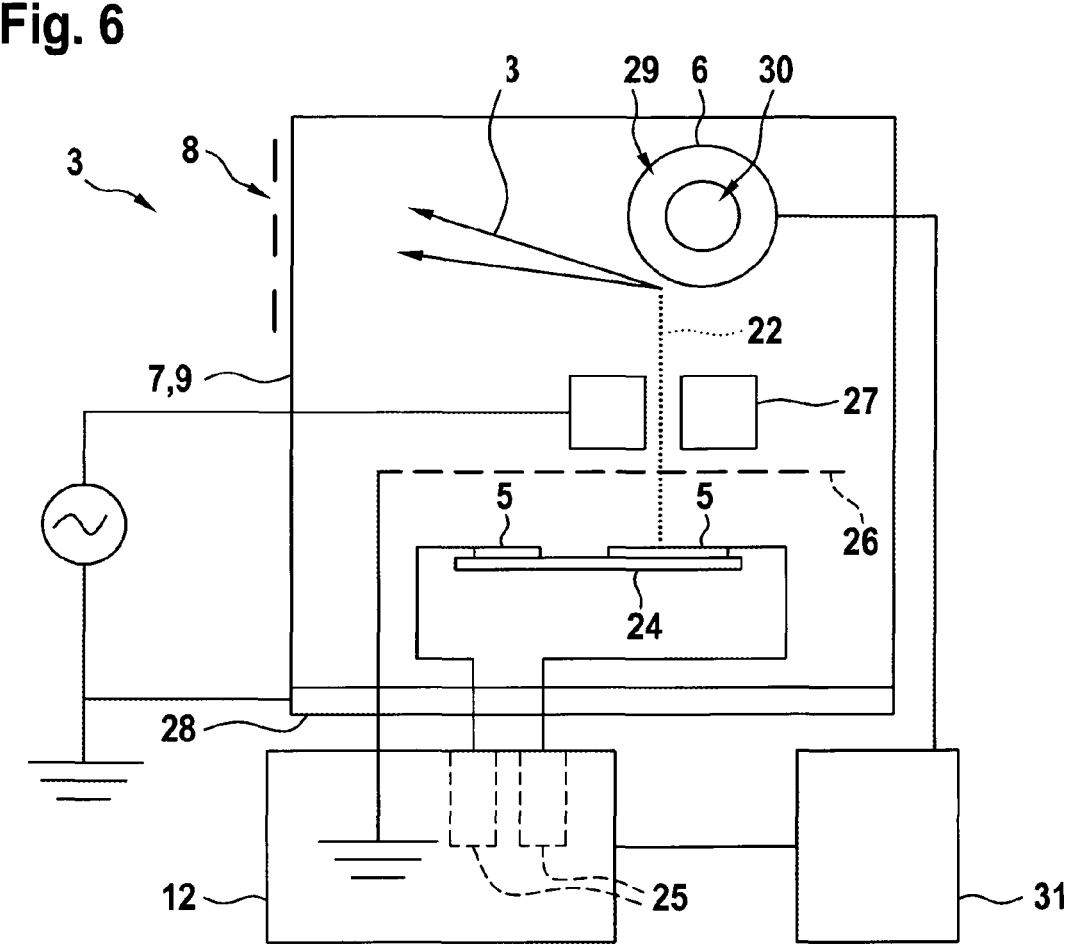
FIG. 6 shows a schematic view of features of a MBFEX tube 9 of a computer tomograph 1 including the associated control system.

Deviating from the exemplary embodiment shown in FIG. 6, which has a passive focusing electrode 27, the X-ray emitter 3 can also be operated with an active focusing electrode 27. In any case, the electron beam 22 is focused such that a focusing effect into several directions is produced.

The anode 6 onto which the electron beam 22 impinges is designed as a rotating, oil-cooled anode. A coolant, which is a conductive oil, flows through an outer duct 29 into the anode 6 and through an inner duct 30 out of the anode 6. The ducts 29, 30 are concentrically arranged in the anode 6. The ducts 29, 30 are conducted through the tube housing 28 of the MBFEX tube 9 in a manner not shown. If the anode 6 has a generally straight rod-like shape, it can be configured as a rotating anode in a deviating embodiment, wherein the central axis of the anode is at the same time the axis of rotation.

The anode 6 is connected to an anode control 31, which both ensures the power supply of the anode 6 and provides the value of the anode current. This value is passed on to the separate electronic multichannel control system 12 according to FIG. 6, thus forming a closed-loop control circuit which implements a current-based current control of the X-ray emitter 3. Electric currents flowing off through the extraction grid 26 and through the focusing electrode 27 are taken into account in this control system.

Figure 7:
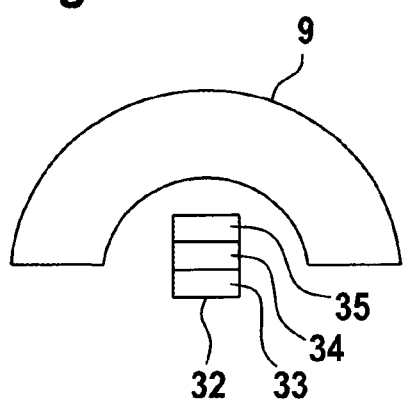
FIG. 7 shows a view according to FIG. 3 of an X-ray emitter 3 of a computer tomograph 1 and an object to be examined.

FIG. 7 outlines the potential position of an examination object 32 relative to the MBFEX tube 9. The examination object 32 comprises various volume regions 33, 34, 35. The distribution of X-ray absorbing material within the volume regions 33, 34, 35 is variable, as outlined in FIG. 8. Potential projection directions in which projection images of the examination object 32 can be taken are visualized by arrows in FIG. 8.

Figure 8:
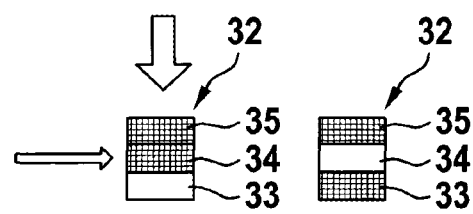
FIG. 8 shows two different states of the object to be examined using the arrangement according to FIG. 7.

FIG. 8 outlines a first state of the examination object 32 on the left and a second state thereof on the right. As can be seen from the symbolized representations, the state shown on the left shows dense material, that is, material strongly absorbing X-ray radiation, in volume regions 34 and 35. In the second state of the examination object 32, such material is exclusively distributed in volume regions 33 and 35.

Otherwise, the examination object 32 is substantially free of X-ray radiation absorbing material.

If a projection image of the examination object 32 is generated with a vertical projection direction relative to the arrangement shown in FIGS. 7 and 8, the change from the first to the second state is not recognizable. But this change is fully visible if the projection direction is horizontal. This is taken into account when operating the computer tomograph 1 in that, when controlling various cathodes 5, such cathodes 5 are activated more frequently which bring out changes of the examination object 32 particularly clearly. The cathodes 5 are selected automatically while the radiogram of the examination object 32 is taken, based on constantly performed image analysis.

Figure 9:
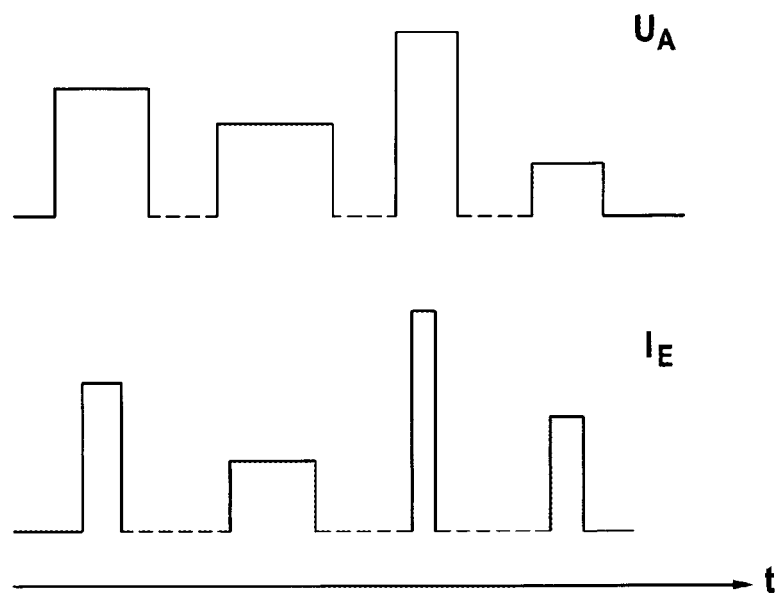
FIG. 9 is a diagram showing the change of the emission current and anode voltage parameters of the computer tomograph 1 according to FIG. 6.

FIG. 9 illustrates options of varying both the anode voltage $U_A$, which is applied to the anode 6, and the emitter current $I_E$, which starts from a cathode 5. The time scale relating to the pulsed operation of the X-ray emitter 3 in FIG. 9 is designated t as usual and refers both to the anode voltage $U_A$ and the emitter current $I_E$. In a total of four pulses, the anode voltage $U_A$ in the case shown is 100 kV, 80 kV, 140 kV, and 60 kV, and the emitter current $I_E$ is 1 A, 0.5 A, 2 A, and 0.8 A. Very fast change of the anode voltage $U_A$ and the emitter current $I_E$ allows multi-energy radiograms of an examination object 32.

Figure 10:
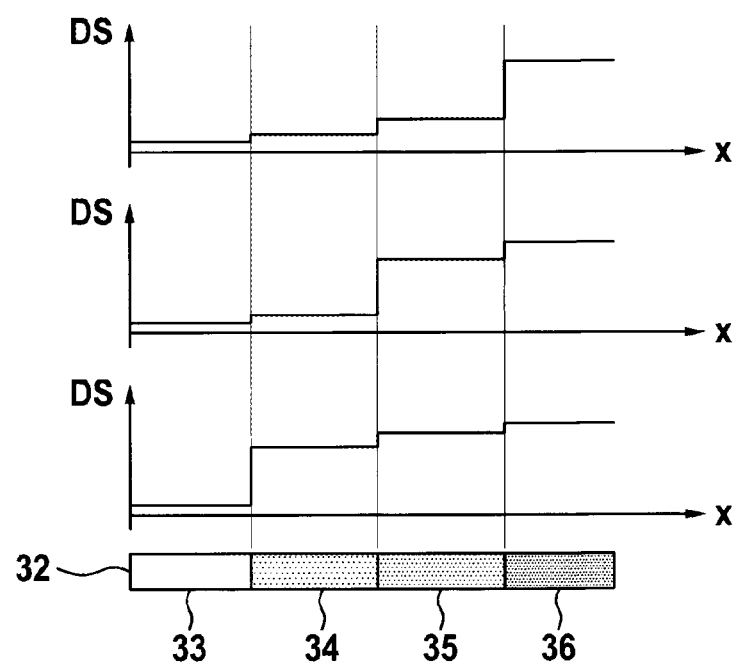
FIG. 10 is a diagram showing the dependency of a detector signal of physical properties of an examination object recorded using a computer tomograph 1 according to FIG. 6 at three different settings of the X-ray emitter 3.

In the case of FIG. 10, an examination object 32 has four different volume regions 33, 34, 35, 36 with increasing density. A detector signal detected with the X-ray detector 3 is referenced as DS. It provides information about the absorption of the X-ray radiation, which is typically specified in Hounsfield units. According to FIG. 10, radiograms are produced with three different energy settings of the emitted X-ray radiation. In each of the three cases, another contour of the examination object 32 is particularly well visible, as is illustrated in the three diagrams shown in FIG. 10, which are referring to a joint position axis. Overall, radiograms of particularly high quality can be generated using the computer tomograph 1.

LIST OF REFERENCE SYMBOLS

1 Computer tomograph
2 Gantry
3 X-ray emitter
4 X-ray detector
5 Cathode
6 Anode
7 Vacuum tube
8 X-ray window
9 MBFEX tube
10 Detector assembly
11 Device base
12 Electronic multichannel control system
13 X-ray fan beam
14 Holder
15 Pivot point
16 Locking device
17 Displacement device
18 Lifting device
19 Housing
20 Castors
21 Screen
22 Electron beam
23 Row
24 Circuit board
25 Emitter control
26 Extraction grid 27 Focusing electrode
28 Tube housing
29 Outer duct
30 Inner duct
31 Anode control
32 Examination object
33 Volume region
34 Volume region
35 Volume region
36 Volume region
DS Detector signal
e Principal emission direction
$I_E$ Emitter current
$U_A$ Anode voltage
z Central axis

The invention claimed is:

1. A computer tomograph for X-ray imaging, comprising a rotationally fixed gantry, in which a plurality of X-ray emitters, radiation influencers, and X-ray detectors is distributed in a fixed manner about a central geometrical axis, wherein said X-ray emitters and X-ray detectors are opposite to one another and offset with respect to each other in a direction of the central axis, and wherein the X-ray emitters have cathodes as electron emitters, the cathodes being separately connected to emitter controls and cooperate with a common extraction grid connected upstream of at least one focusing electrode as a radiation inducer;

wherein the emitter controls operate the plurality of X-ray emitters, radiation influencers and X-ray detectors to generate a first set of projection images taken from different projection directions and to take at least one additional set of projection images from additional projection directions, wherein the additional projection directions at least partially match the projection directions of the first set of projection images;

wherein the emitter controls determine a similarity level between two projection images taken from matching projection directions; and wherein frequency of selected projection directions depends on the similarity level of projection images taken from the respective projection directions at subsequent points in time.

2. The computer tomograph according to claim 1, wherein the gantry is displaceable only in the direction of the central axis.

3. The computer tomograph according to claim 1, wherein the X-ray emitters and the X-ray detectors fully enclose the central axis.

4. The computer tomograph according to claim 3, wherein the X-ray emitters and the X-ray detectors are arranged on a circle.

5. The computer tomograph according to claim 3, wherein the X-ray emitters and the X-ray detectors are arranged in at least three rows of equal length, wherein said rows form a regular polygon.

6. The computer tomograph according to claim 1, wherein the X-ray emitters comprise nanorod-containing cathodes for field emission of electrons.

7. The computer tomograph according to claim 6, wherein the X-ray emitters include carbon nanotubes as nanorods.

8. The computer tomograph according to claim 1, wherein the X-ray detectors comprise direct solid-state detectors for detecting X-ray radiation.

9. The computer tomograph according to claim 1, wherein at least eight cathodes are assigned to a common extraction grid.

10. The computer tomograph according to claim 1, comprising at least two different cathodes.

11. The computer tomograph according to claim 1, comprising a rigid, liquid-cooled anode.

12. A method for operating a computer tomograph, comprising a rotationally fixed gantry in which a plurality of X-ray emitters, radiation influencers, and X-ray detectors are rigidly arranged, wherein the X-ray emitters comprise multiple electron emitters cooperating with a common anode, and in which slice images are generated from projection images of a changing examination object, having the following features:

Generating a first set of projection images taken from different projection directions, Taking at least one additional set of projection images from additional projection directions, wherein the additional projection directions at least partially match the projection directions of the first set of projection images, Determining the level of similarity between two projection images taken from matching projection directions, Generating other projection images, wherein frequency of selected projection directions depends on a level of similarity of projection images taken from the respective projection directions at subsequent points in time.

13. The method according to claim 12, wherein projection images are created from a specific projection direction, wherein the more frequently the lower a level of similarity between projection images taken from the respective projection direction is at subsequent points in time.

14. The method according to claim 12, wherein both an emission current ($I_E$) of the electron emitter and anode voltage ($U_A$) are varied in successive X-ray pulses.

15. The method according to claim 14, wherein the X-ray radiation emitted is varied by at least 100 steps in wavelength and dose per pulse during examination of an examination object.

* * * * *